United States Patent [19]

Umezawa et al.

[11] 4,406,891
[45] Sep. 27, 1983

[54] N-METHANESULFONIC ACID DERIVATIVES OF ISTAMYCIN A OR B AND PRODUCTION THEREOF

[75] Inventors: Hamao Umezawa, Tokyo; Shinichi Kondo, Yokohama, both of Japan

[73] Assignee: Zaidan Hojin Biseibutsu Kagaku Kenkyu Kai, Tokyo, Japan

[21] Appl. No.: 289,963

[22] Filed: Aug. 4, 1981

[30] Foreign Application Priority Data

Aug. 22, 1980 [JP] Japan ................................ 55-114685

[51] Int. Cl.$^3$ ....................... A61K 31/71; C07H 15/22
[52] U.S. Cl. ................................... 424/180; 536/16.1; 536/16.8; 424/181
[58] Field of Search ............... 424/180; 536/17 R, 10, 536/16.1, 16.8

[56] References Cited

U.S. PATENT DOCUMENTS

| 4,091,202 | 5/1978 | Umezawa et al. | 536/10 |
|---|---|---|---|
| 4,250,304 | 2/1981 | Martin et al. | 536/17 R |
| 4,273,924 | 6/1981 | Martin et al. | 536/17 R |
| 4,276,413 | 6/1981 | Martin et al. | 536/17 R |
| 4,283,529 | 8/1981 | Rosenbrook, Jr. | 536/17 R |
| 4,296,106 | 10/1981 | Umezawa et al. | 536/17 R |

*Primary Examiner*—Johnnie R. Brown
*Attorney, Agent, or Firm*—Lalos, Leeds, Keegan, Lett & Marsh

[57] ABSTRACT

As new semi-synthetic antibiotic derivative are provided N-methanesulfonic acid derivatives of istamycin A or B which are lower toxic than the parent antibiotic and retain usefully high antibacterial activity. They are produced by N-sulfomethylation in such way that istamycin A or B is reacted with an aldehyde such as paraformaldehyde and sulfurous acid or sulfite reagent.

8 Claims, No Drawings

N-METHANESULFONIC ACID DERIVATIVES OF ISTAMYCIN A OR B AND PRODUCTION THEREOF

SUMMARY OF THE INVENTION

This invention relates to a less toxic derivative of istamycin A or B, and in particular, an istamycin A or B N-methanesulfonic acid derivative which is a new compound valuable for use in therapeutic treatment of bacterial infections. This invention further relates to a process for the preparation of such lower toxic derivative of istamycin A or B.

BACKGROUND OF THE INVENTION

Istamycin A or B is a new aminoglycosidic antibiotic discovered by the present inventors and is represented by the formula:

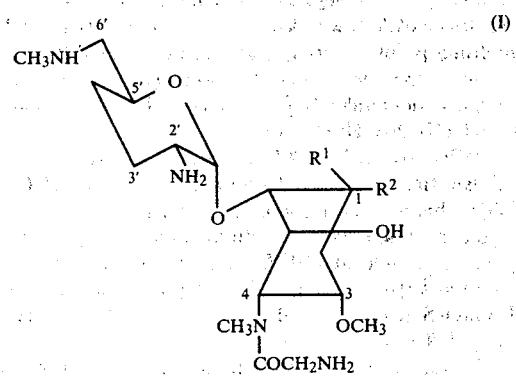

wherein $R^1$ is a hydrogen atom and $R^2$ is an amino group for istamycin A, or $R^1$ is an amino group and $R^2$ is a hydrogen atom for istamycin B (see Japanese Patent Application "Kokai" No. 145697/80; U.K. Patent Application GB 2048855A; U.S. Patent Application Ser. No. 141,492 now U.S. Pat. No. 4,296,106). Istamycin A or B is known to exhibit a high antibacterial activity against a wide range of gram-negative and gram-positive bacteria.

It is also known that a few of aminoglycosidic antibiotic substances are converted to an N-methanesulfonic acid derivative thereof by N-sulfomethylation of some or all of the amino group(s) present in the molecule, and that the N-methanesulfonic acid derivative so produced exhibits a lower toxicity than the parent antibiotic. An example of this is N-methanesulfonic acid derivatives of kanamycin A (Journal of Antibiotics, A 14, page 170 (1961)). Besides, it has been found by the present inventors that an N-methanesulfonic acid derivaive of 3',4'-dideoxykanamycin B can be synthetized by interaction of 3',4'-dideoxykanamycin B, an aldehyde and sulfurous acid or an alkali metal hydrogen sulfite, and that this N-methanesulfonic acid derivative is of lower toxicity than 3',4'-dideoxykanamycin B and hence is valuable for therapeutic treatment of bacterial infections (see Japanese Patent Application "Kokai" No. 39653/77; U.K. Patent No. 1507118; U.S. Pat. No. 4,091,202). Recently, it has also been reported that a less toxic N-methanesulfonic acid derivative of fortimycin antibiotic may be obtained as a new substance having useful antibacterial activity (see Japanese Patent Application No. 38301/80).

Accordingly, if a new antibiotic derivative of istamycin A or B which shows a lower toxicity than istamycin A or B itself is provided, it will increase the applications of istamycin A or B and make this antibiotic substance more valuable.

An object of this invention is to provide a new antibiotic derivative of istamycin A or B which retains the useful antibacterial activity of istamycin A or B but exhibits a lower toxicity than that of istamycin A or B. The other object is to provide a process for the preparation of such new antibiotic derivative of istamycin A or B. Another objects of this invention will be clear from the following descriptions.

As a result of extensive research, we, the present inventors, have now found that as new compounds, N-methanesulfonic acid derivatives of istamycin A or B can be synthetized by reaction of istamycin A or B of the above formula (I) with an aldehyde of the formula:

wherein R is as defined later and also with sulfurous acid or an alkali or alkaline earth metal hydrogen sulfite (including ammonium hydrogen sulfite) of the formula:

wherein M is a hydrogen atom, an alkali metal, alkaline earth metal atom or ammonium cation. We have confirmed that these N-methanesulfonic acid derivatives of istamycin A or B are of remarkedly lower toxicity than istamycin A or B. Istamycin A or B contains three amino groups and one methylamino group per molecule as will be clear from the above formula (I), and it has been found that the new N-methanesulfonic acid derivative of istamycin A or B prepared is the one in which one, two, three or four groups amongst the aforesaid three amino groups and one methylamino group present in the molecule is (are) N-sulfomethylated, that is to say, substituted with a methanesulfonate group of the formula:

wherein R is a hydrogen atom, an alkyl group, preferably an alkyl group of 1~4 carbon atoms, a substituted alkyl group, phenyl group or a substituted phenyl group, and M represents a hydrogen atom, an ammonium cation, an alkali metal or an alkaline earth metal atom. The total number of the N-sulfomethylated amino and methylamino groups present in the resulting N-methanesulfonic acid derivative of istamycin A or B amounts to 1, 2, 3 or 4, depending upon the molar proportions of the aldehyde and the sulfurous acid or sulfite compound employed for 1 molar proportion of istamycin A or B.

DETAILED DESCRIPTION OF THE INVENTION

According to a first aspect of this invention, there is provided as a new compound, an N-methanesulfonic acid derivative of istamycin A or B of the formula:

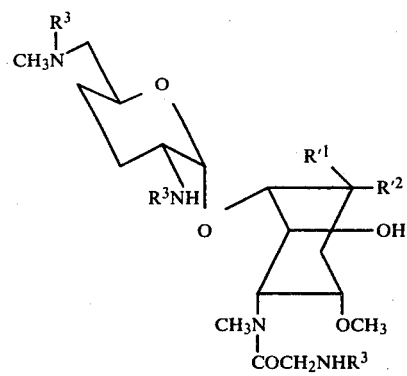

(I')

wherein R$^{1'}$ is a hydrogen atom and R$^{2'}$ is a group —NHR$^3$, or R$^{1'}$ is a group —NHR$^3$ and R$^{2'}$ is a hydrogen atom, and one, two, three or four of the R$^3$ groups represent(s) each a group —CHRSO$_3$M and the other R$^3$ groups represent(s) each a hydrogen atom where R is a hydrogen atom, an alkyl group, a substituted alkyl group, phenyl group or a substituted phenyl group, and M is a hydrogen atom, an ammonium cation, an alkali metal atom or an alkaline earch metal atom.

When R in the group —CHRSO$_3$M shown above denotes an alkyl group, it may preferably be a lower alkyl containing 1 to 4 carbon atoms, such as methyl, ethyl, n-butyl and n-propyl. R may also be a substituted alkyl group such as a lower alkyl bearing one or more methoxy or chloro substitutents thereon. Suitable examples of the substituted alkyl group include methoxymethyl, monochloromethyl and dichloromethyl. When R is a substituted phenyl group, it may be, for example, p-methoxyphenyl and o-hydroxyphenyl. According to a particular embodiment of the first aspect invention, there is provided an N-methanesulfonic acid derivative of istamycin A or B which is an istamycin A di-N-methanesulfonic acid disodium salt derivative of the formula (I') where R$^{1'}$ is a hydrogen atom, R$^{2'}$ is a group —NHR$^3$, two R$^3$ groups represent each a group —CH$_2$SO$_3$Na and the remaining two R$^3$ groups represent each a hydrogen atom; an istamycin A tri-N-methanesulfonic acid trisodium salt derivative of the formula (I') where R$^{1'}$ is a hydrogen atom, R$^{2'}$ is a group —NHR$^3$, three R$^3$ groups represent each a group —CH$_2$SO$_3$Na and the remaining one R$^3$ groups represents a hydrogen atom; an istamycin A tetra-N-methanesulfonic acid tetrasodium salt derivative of the formula (I') where R$^{1'}$ is a hydrogen atom, R$^{2'}$ is a group —NHR$^3$ and all four R$^3$ groups represent each a group —CH$_2$SO$_3$Na; an istamycin B di-N-methanesulfonic acid disodium salt derivative of the formula (I') where R$^{1'}$ is a group —NHR$^3$, R$^{2'}$ is a hydrogen atom, two R$^3$ groups represent each a group —CH$_2$SO$_3$Na and the remaining two R$^3$ groups represent each a hydrogen atom; an istamycin B tri-N-methanesulfonic acid trisodium salt derivative of the formula (I') where R$^{1'}$ is a group —NHR$^3$, R$^{2'}$ is a hydrogen atom, three R$^3$ groups represent each a group —CH$_2$SO$_3$Na and the remaining one R$^3$ group represents a hydrogen atom; or an istamycin B tetra-N-methanesulfonic acid tetrasodium salt derivative of the formula (I') where R$^{1'}$ is a group —NHR$^3$, R$^{2'}$ is a hydrogen atom and all four R$^3$ groups represent each a group —CH$_2$SO$_3$Na.

Particular examples of the new istamycin A or B N-methanesulfonic acid derivative obtained according to the invention are listed below together with physicochemical properties thereof:

(1) Istamycin A-di-N-methanesulfonic acid disodium salt of the following formula: C$_{17}$H$_{33}$N$_5$O$_5$(CH$_2$SO$_3$Na)$_2$ This new compound is in the form of a colorless powder which has no definite melting point, decomposes gradually at 213° C. and shows a specific optical rotation $[\alpha]_D^{25}+71°$ (c 1, water). Elemental analysis thereof is as follows: Found: S 11.10%; Calcd. for C$_{17}$H$_{33}$N$_5$O$_5$(CH$_2$SO$_3$Na)$_2$: S 10.31%.

(2) Istamycin A-tri-N-methanesulfonic acid trisodium salt of the following formula: C$_{17}$H$_{32}$N$_5$O$_5$(CH$_2$SO$_3$Na)$_3$ This new compound is in the form of a colorless powder which has no definite melting point, decomposes gradually at 240° C. and shows a specific optical rotation $[\alpha]_D^{25}+67°$ (c 1, water). Elemental analysis: Found: S 12.95%; Calcd. for C$_{17}$H$_{32}$N$_5$O$_5$(CH$_2$SO$_3$Na)$_3$: S 13.02%. (3) Istamycin A-tetra-N-methanesulfonic acid tetrasodium salt of the following formula: C$_{17}$H$_{31}$N$_5$O$_5$(CH$_2$SO$_3$Na)$_4$ This new compound is in the form of a colorless powder which has no definite melting point, decomposes gradually at 225° C. and shows a specific optical rotation $[\alpha]_D^{25}+62°$ (c 1, water). Elemental analysis: Found: S 13.23%; Calcd. for C$_{17}$H$_{31}$N$_5$O$_5$(CH$_2$SO$_3$Na)$_4$: S 14.99%.

(4) Istamycin B-di-N-methanesulfonic acid disodium salt of the following formula: C$_{17}$H$_{33}$N$_5$O$_5$(CH$_2$SO$_3$Na)$_2$ This new compound is in the form of a colorless powder which has no definite melting point, decomposes gradually at 260° C. and shows a specific optical rotation $[\alpha]_D^{24}+75°$ (c 0.5, water). Elemental analysis: Found S 10.04%; Calcd. for C$_{17}$H$_{33}$N$_5$O$_5$(CH$_2$SO$_3$Na)$_2$: S 10.31%.

(5) Istamycin B-tri-N-methanesulfonic acid trisodium salt of the following formula: C$_{17}$H$_{32}$N$_5$O$_5$(CH$_2$SO$_3$Na)$_3$ This new compound is in the form of a colorless powder which has no definite melting point, decomposes gradually at 240° C. and shows a specific optical rotation $[\alpha]_D^{24}+63°$ (c 1, water). Elemental analysis: Found: S 13.40%; Calcd. for C$_{17}$H$_{32}$N$_5$O$_5$(CH$_2$SO$_3$Na)$_3$: S 13.02%.

(6) Istamycin B-tetra-N-methanesulfonic acid tetrasodium salt of the following formula: C$_{17}$H$_{31}$N$_5$O$_5$(CH$_2$SO$_3$Na)$_4$ This new compound is in the form of a colorless powder which has no definite melting point, decomposes gradually at 234° C. and shows a specific optical rotation $[\alpha]_D^{27}+57°$ (c 1, water). Elemental analysis: Found: S 14.92%; Calcd. for C$_{17}$H$_{31}$N$_5$O$_5$(CH$_2$SO$_3$Na)$_4$: S 14.99%.

Each of the above new compounds is a colorless powder having no definite melting point, which is readily soluble in water, sparingly soluble in a lower alkanol such as methanol, ethanol and 1-butanol, tetrahydrofuran, dioxane and N,N-dimethylformamide but insoluble in benzene and ethyl ether.

The N-methanesulfonic acid derivatives of istamycin A and of istamycin B according to the invention exhibit high antibacterial activity against a wide variety of bacteria, as much as that of istamycin A and istamycin B themselves. For example, there are shown below minimum inhibitory concentrations (mcg/ml) of istamycin B-tri-N-methanesulfonic acid trisodium salt and istamycin B-tetra-N-methanesulfonic acid tetrasodium salt to various bacteria which have been estimated according to a standard serial dilution method using nutrient agar as the incubation medium, the incubation being made at 37° C. for 17 hours. Minimum inhibitory concentrations of the parent antibiotics, istamycin A and istamycin B themselves were estimated in the same manner for the comparison purpose. The antibacterial spectra so obtained are shown in Table 1 below.

A test compound was dissolved in 0.25 ml of a physiological saline solution and the solution of the test compound so prepared was intravenously administered into

TABLE 1

Antibacterial spectra of N—methanesulfonic acid derivatives of istamycin B

| Test Microorgansims | Minimum Inhibitory Concentrations (mcg/ml) | | | |
|---|---|---|---|---|
| | Istamycin B-tri-N—methanesulfonic acid Na salt | Istamycin B-tetra-N—methanesulfonic acid Na salt | Istamycin A (comparative) | Istamycin B (comparative) |
| Staphylococcus aureus 209P | 0.78 | 0.78 | 0.78 | 0.39 |
| Staphylococcus aureus Smith | <0.20 | 0.39 | <0.20 | <0.20 |
| Staphylococcus aureus Ap01 | 1.56 | 1.56 | 0.78 | 0.78 |
| Staphylococcus epidermidis 109 | 1.56 | 1.56 | 0.78 | 0.78 |
| Micrococcus flavus FDA 16 | 50 | 100 | 3.13 | 6.25 |
| Sarcina lutea PCI 1001 | 0.20 | 0.39 | 0.20 | 0.20 |
| Bacillus anthracis | 0.39 | 0.39 | <0.20 | <0.20 |
| Bacillus subtilis PCI 219 | 0.39 | 0.39 | <0.20 | <0.20 |
| Bacillus subtilis NRRLB-558 | 0.39 | 0.78 | 0.39 | <0.20 |
| Bacillus cereus ATCC 10702 | 6.25 | 6.25 | 3.13 | 1.56 |
| Corynebacterium bovis 1810 | 12.5 | 6.25 | 1.56 | 0.78 |
| Mycobacterium smegmatis ATCC 607 | 0.78 | 1.56 | 1.56 | 0.78 |
| Escherichia coli NIHJ | 3.13 | 3.13 | 3.13 | 1.56 |
| Escherichia coli K-12 | 6.25 | 6.25 | 1.56 | 1.56 |
| Escherichia coli K-12 R5 | 6.25 | 12.5 | 3.13 | 3.13 |
| Escherichia coli K-12 R388 | 3.13 | 6.25 | 0.78 | 1.56 |
| Escherichia coli K-12 J5R11-2 | 6.25 | 6.25 | 3.13 | 1.56 |
| Escherichia coli K-12 ML1629 | 6.25 | 6.25 | 3.13 | 1.56 |
| Escherichia coli K-12 ML1630 | 6.25 | 6.25 | 3.13 | 1.56 |
| Escherichia coli K-12 ML1410 | 3.13 | 6.25 | 3.13 | 3.13 |
| Escherichia coli K-12 ML1410 R81 | 3.13 | 6.25 | 1.56 | 1.56 |
| Escherichia coli K-12 LA290 R55 | 6.25 | 6.25 | 3.13 | 1.56 |
| Escherichia coli K-12 LA290 R56 | 3.13 | 6.25 | 1.56 | 1.56 |
| Escherichia coli K-12 LA290 R64 | 3.13 | 6.25 | 1.56 | 1.56 |
| Escherichia coli W677 | 3.13 | 3.13 | 1.56 | 0.78 |
| Escherichia coli JR66/W677 | 6.25 | 6.25 | 3.13 | 3.13 |
| Escherichia coli K-12 C600 R135 | 25 | 50 | >100 | 12.5 |
| Escherichia coli JR225 | 3.13 | 3.13 | 1.56 | 0.78 |
| Klebsiella pneumoniae PCI602 | 3.13 | 3.13 | 1.56 | 1.56 |
| Klebsiella pneumoniae 22#3038 | 6.25 | 12.5 | 3.13 | 3.13 |
| Shigella dysenteriae JS11910 | 6.25 | 12.5 | 3.13 | 3.13 |
| Shigella flexneri JS11811 | 6.25 | 12.5 | 6.25 | 3.13 |
| Shigella sonnei JS11756 | 6.25 | 12.5 | 6.25 | 3.13 |
| Salmonella typhi T-63 | 6.25 | 3.13 | 0.78 | 0.78 |
| Salmonella enteritidis 1891 | 6.25 | 6.25 | 3.13 | 1.56 |
| Proteus vulgaris OX19 | 1.56 | 1.56 | 0.78 | 0.39 |
| Proteus rettgeri GN311 | 25 | 50 | 25 | 12.5 |
| Proteus rettgeri GN466 | 12.5 | 12.5 | 6.25 | 3.13 |
| Serratia marcescens | 12.5 | 25 | 6.25 | 3.13 |
| Serratia SOU | >100 | >100 | >100 | >100 |
| Serratia 4 | >100 | >100 | 50 | 6.25 |
| Providencia Pv16 | 25 | 25 | 6.25 | 25 |
| Providencia 2991 | 25 | 25 | 25 | 12.5 |
| Pseudomonas aeruginosa A3 | 12.5 | 12.5 | 6.25 | 1.56 |
| Pseudomonas aeruginosa No. 12 | >100 | >100 | 100 | 12.5 |
| Pseudomonas aeruginosa H9 | 100 | 100 | 25 | 12.5 |
| Pseudomonas aeruginosa H11 | >100 | >100 | 100 | 25 |
| Pseudomonas aeruginosa TI-13 | 100 | 100 | 25 | 6.25 |
| Pseudomonas aeruginosa GN315 | 50 | 100 | 25 | 6.25 |
| Pseudomonas aeruginosa 99 | >100 | >100 | >100 | 100 |
| Pseudomonas aeruginosa B-13 | >100 | >100 | >100 | >100 |
| Pseudomonas aeruginosa 21-75 | >100 | >100 | >100 | 25 |
| Pseudomonas aeruginosa PST1 | >100 | >100 | 100 | 25 |
| Pseudomonas aeruginosa ROS134/PU21 | >100 | >100 | 100 | 50 |
| Pseudomonas aeruginosa K-Ps102 | 100 | 100 | 50 | 12.5 |
| Pseudomonas maltophilis GN907 | >100 | >100 | >100 | >100 |

The N-methanesulfonic acid derivatives of istamycin A and of istamycin B according to this invention have a remarkedly reduced acute toxicity, as compared to istamycin A and istamycin B themselves, notwithstanding that the former compounds retain high antibacterial activity against various bacteria.

Acute toxicity of the various N-methanesulfonic acid derivatives of istamycin A and of istamycin B of the invention has been determined by the following procedure:

a series of mouse groups each consisting of six mice (ICR strain, adult female, body weight 20 g ±0.5 g) as the test animal, so that the test compound was given to each mouse at a dosage of 1000 mg/kg. Acute toxicity of istamycin A and istamycin B was also estimated in the same manner as above for the comparison purpose. It was then observed that all mice survived for more than two weeks when the N-methanesulfonic acid derivatives of istamycin A and of istamycin B were administered at a dosage of 1000 mg/kg ($LD_{50}$>1000 mg/kg), whereas all mice died within 24 hours when istamycin A or B (comparative) was administered at a dosage of 200 mg/kg (LD$_{50}$ 100~200 mg/kg).

From the test results of Table 1 and of acute toxicity as mentioned above, it is evident that the new compounds of the invention have remarkedly reduced toxicity but retain usefully high antibacterial activity against various bacteria.

The new compounds of the invention are effective in the treatment of bacterial infections when administered intramuscularly in the dosage range of about 100 mg to about 2000 mg per day in divided doses three or four times a day. Generally the new compounds may be administered orally, intraperitoneally, intravenously or intramuscularly using any pharmaceutical form known to the art for such administration and in a similar manner to kanamycins. Examples of pharmaceutical forms for oral administration are powders, capsules, tablets, syrup and the like.

The new N-methanesulfonic acid derivatives of istamycin A or B of the above formula (I') according to the invention may be prepared by reaction of istamycin A or B, either in the form of the free base or an acid addition salt thereof, with an aldehyde of the formula:

RCHO                                                           (III)

wherein R is a hydrogen atom, an alkyl group, particularly a lower alkyl group of 1~4 carbon atoms, a substituted alkyl group, phenyl group or a substituted phenyl group, and sulfurous acid or a sulfite of the formula:

MHSO$_3$                                               (IV)

wherein M is a hydrogen atom, an ammonium cation, an alkali metal atom or an alkaline earth metal atom. The resulting N-methanesulfonic acid derivatives contains a number of the N-methanesulfonate group(s) which takes varying value of 1, 2, 3 or 4 depending upon the molar proportions of the aldehyde and the sulfurous acid or sulfite compound employed for 1 molar proportion of istamycin A or B. The aldehyde and the sulfurous acid or sulfite may be reacted simultaneously with istamycin A or B, or alternatively either one of the aldehyde reagent and the sulfurous acid or sulfite reagent may be reacted at first with istamycin A or B before the resulting reaction product is reacted with the other reagent.

According to a second aspect of the present invention, therefore, there is provided a process for the preparation of an N-methanesulfonic acid derivative of istamycin A or B of the formula:

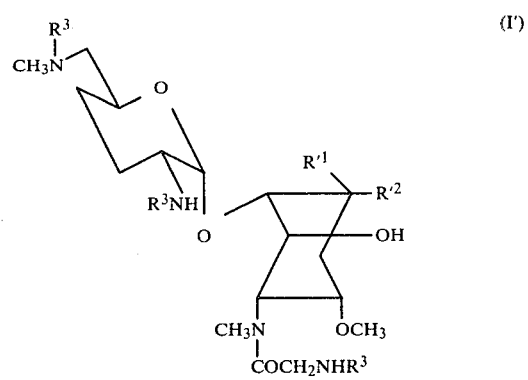

wherein R$^{1'}$ is a hydrogen atom and R$^{2'}$ is a group —NHR$^3$, or R$^{1'}$ is a group —NHR$^3$ and R$^{2'}$ is a hydrogen atom, and one, two, three or four of the R$^3$ groups represent(s) each a group —CHRSO$_3$M and the other R$^3$ groups represent(s) each a hydrogen atom where R is a hydrogen atom, an alkyl group, a substituted alkyl group, phenyl group or a substituted phenyl group, and M is a hydrogen atom, an ammonium cation, an alkali metal atom or an alkaline earth metal atom, which comprises reacting istamycin A or B (free base) or an acid addition salt thereof with an aldehyde of the formula:

RCHO                                                      (III)

wherein R is as defined above and sulfurous acid or a sulfite of the formula:

MHSO$_3$                                               (IV)

wherein M is as defined above.

When sulfurous acid of the above formula (IV) where M is a hydrogen atom is used as one of the reagents in the process of the invention it may conveniently be used in the form of gaseous sulfur dioxide. However, it is feasible, of course, to employ aqueous sulfurous acid. Instead of the sulfurous acid reagent, an alkali metal, alkaline earth metal or ammonium hydrogen sulfite may be used as an equivalent agent. Sodium hydrogen sulfite, potassium hydrogen sulfite, lithium hydrogen sulfite and ammonium hydrogen sulfite are suitable as the sulfite for the purpose of the invention. Suitable examples of the aldehyde reagent of the formula (III) available for the invention include paraformaldehyde, acetaldehyde, methoxyacetaldehyde, monochloroacetaldehyde, dichloroacetaldehyde, glyoxal, propionaldehyde, n-butylaldehyde, benzaldehyde, p-methoxybenzaldehyde and salicylaldehyde.

In preparing the new compound of the above formula (I') according to the invention, either one of the aldehyde reagent of the formula (III) and the sulfurous acid or sulfite reagent of the formula (IV) may be reacted at first with istamycin A or B. Thus, it is feasible to carry out the process in such a manner that the aldehyde reagent is reacted at first with istamycin A or B to produce the corresponding Schiff's base so formed, this Schiff's base is isolated and then reacted with the sulfurous acid or sulfite reagent to yield the desired istamycin A or B N-methanesulfonic acid derivative (I') as the final product. Alternatively, it is possible to conduct the process in such a manner that the sulfurous acid or sulfite reagent is at first reacted with istamycin A or B to convert the latter into the form of an acid-addition salt with sulfurous acid, which is subsequently reacted with the aldehyde reagent to yield the desired N-methanesulfonic acid derivative (I') as the final product. Moreover, an adduct of both the reagents (III) and (IV) such as sodium hydroxymethanesulfonate or glyoxal sodium hydrogen sulfite may also be used in the process of the invention. Namely, this adduct may be directly reacted with istamycin A or B to yield the desired N-methanesulfonic acid derivative (I') as the final product.

As will be clear from the above, the molar proportions of the aldehyde reagent and the sulfurous acid or sulfite reagent to be interacted with istamycin A or B may vary from 1 molar to 4 molar proportions for 1 molar proportion of istamycin A or B. The N-methanesulfonic acid derivatives obtained as the final product by the process of the invention contain the methanesulfonate component at different contents depending on the molar proportions of the aldehyde reagent and the sulfurous acid or sulfite reagent employed, but usually contain one, two, three or four N-methanesulfonate groups per molecule of istamycin A or B.

Generally, the process may be carried out preferably using water as the reaction medium, but a small proportion of a lower alcohol such as methanol and ethanol may be added to the reaction medium when the starting aldehyde (III) is hardly soluble in water. The process may readily be conducted at a temperature of 0° to 70° C. for a reaction period of usually 0.5 to 24 hours.

For recovery of the final product from the reaction solution, it may be precipitated as a colorless deposit by adding thereto a volume of such an organic solvent in which the desired product is sparingly soluble, such as a lower alcohol e.g. methanol and ethanol, tetrahydrofuran, dioxane and N,N-dimethylformamide. The colorless precipitate formed is filtered out, washed with methanol or ethanol and then dried to afford the desired istamycin A or B N-methanesulfonic acid derivative (I') in a yield of 55% or more.

That the new derivatives of istamycin A or B as produced by the process of the invention have the molecular structure corresponding to that of an N-methanesulfonic acid derivative has been confirmed from the infrared absorption spectrophotometry as well as from the experiments showing that they liberate formaldehyde when hydrolyzed with diluted hydrochloric acid.

As stated before, the new compounds of the invention are effective in treatment of bacterial infections. According to a third aspect of the invention, therefore, there is provided an antibacterial pharmaceutical composition for treating bacterial infections in a living animal, comprising an antibacterially effective amount of an istamycin A or B N-methanesulfonic acid derivative of the formula (I'), in combination with a pharmaceutically acceptable carrier therefor.

The invention is now illustrated with reference to the following Examples which are in no way limitative for the invention.

EXAMPLE 1

Istamycin A (free base) (38.9 mg; 0.1 millimol) was dissolved in water (0.15 ml), and the resultant aqueous solution was admixed with sodium hydrogen sulfite (20.8 mg; 0.2 mmol) and paraformaldehyde (6 mg; 0.2 mmol). The resulting mixture was shaken overnight at ambient temperature for the reaction. Ethanol (5 ml) was then added to the reaction solution to deposit a colorless precipitate. This precipitate was collected by filtration and dried under reduced pressure to a constant weight, yielding 34.2 mg of the istamycin A-di-N-methanesulfonic acid disodium salt as a colorless powder having no definite melting point but decomposing gradually at 213° C. Yield 55%, $[\alpha]_D^{25} +71°$ (c 1, water).

Elemental analysis: Found: S 11.10%. Calcd. for $C_{17}H_{33}N_5O_5(CH_2SO_3Na)_2$: S 10.31%.

EXAMPLE 2

The process of Example 1 was repeated using 38.9 mg (0.1 mmol) of istamycin A (free base), 0.15 ml of water, 31.2 mg (0.3 mmol) of sodium hydrogen sulfite and 9 mg (0.3 mmol) of paraformaldehyde. Istamycin A-tri-N-methanesulfonic acid trisodium salt (65.4 mg) was obtained as a colorless powder having no definite melting point but decomposing gradually at 240° C. Yield 89%, $[\alpha]_D^{25} +67°$ (c 1, water).

Elemental analysis: Found: S 12.95%. Calcd. for $C_{17}H_{32}N_5O_5(CH_2SO_3Na)_3$: S 13.02%.

EXAMPLE 3

The process of Example 1 was repeated using 38.9 mg (0.1 mmol) of istamycin A free base, 0.15 ml of water, 41.7 mg (0.4 mmol) of sodium hydrogen sulfite and 12 mg (0.4 mmol) of paraformaldehyde. Istamycin A-tetra-N-methanesulfonic acid tetrasodium salt (77.7 mg) was obtained as a colorless powder having no definite melting point but decomposing gradually at 225° C. Yield 91%, $[\alpha]_D^{25} +62°$ (c 1, water).

Elemental analysis Found: S 13.23%. Calcd. for $C_{17}H_{31}N_5O_5(CH_2SO_3Na)_4$: S 14.99%.

EXAMPLE 4

Istamycin B (free base) (38.9 mg; 0.1 millimol) was dissolved in water (0.11 ml), and the resultant aqueous solution was admixed with sodium hydrogen sulfite (20.8 mg; 0.2 mmol) and paraformaldehyde (6 mg; 0.2 mmol). The resulting mixture was shaken overnight at ambient temperature for the reaction. Ethanol (2.4 ml) was then added to the reaction solution to deposit a colorless precipitate. This precipitate was collected by filtration and dried under reduced pressure to a constant weight, yielding 42.5 mg of istamycin B-di-N-methanesulfonic acid disodium salt as a colorless powder having no definite melting point but decomposing gradually at 260° C. Yield 68%, $[\alpha]_D^{24} +75°$ (c 0.5, water).

Elemental analysis: Found: S 10.04%. Calcd. for $C_{17}H_{33}N_5O_5(CH_2SO_3Na)_2$: S 10.31%.

EXAMPLE 5

The process of Example 4 was repeated using 38.9 mg (0.1 mmol) of istamycin B (free base), 0.11 ml of water, 31.2 mg (0.3 mmol) of sodium hydrogen sulfite and 9 mg (0.3 mmol) of paraformaldehyde. Istamycin B-tri-N-methanesulfonic acid trisodium salt (71.7 mg) was obtained as a colorless powder having no definite melting point but decomposing gradually at 240° C. Yield 97%, $[\alpha]_D^{24} +63°$ (c 1, water).

Elemental analysis Found: S 13.40%. Calcd for $C_{17}H_{32}N_5O_5(CH_2SO_3Na)_3$: S 13.02%.

EXAMPLE 6

The process of Example 1 was repeated using 38.9 mg (0.1 mmol) of istamycin B (free base), 0.4 ml of water, 41.7 mg (0.4 mmol) of sodium hydrogen sulfite and 12 mg (0.4 mmol) of paraformaldehyde. Istamycin B-tetra-N-methanesulfonic acid tetrasodium salt (81.8 mg) was obtained as a colorless powder having no definite melting point but decomposing gradually at 234° C. Yield 96%, $[\alpha]_D^{27} +57°$ (c 1, water).

Elemental analysis Found S 14.92%. Calcd. for $C_{17}H_{31}N_5O_5(CH_2SO_3Na)_4$: S 14.99%.

What we claim is:

1. An N-methanesulfonic acid derivative of istamycin A or B of the formula

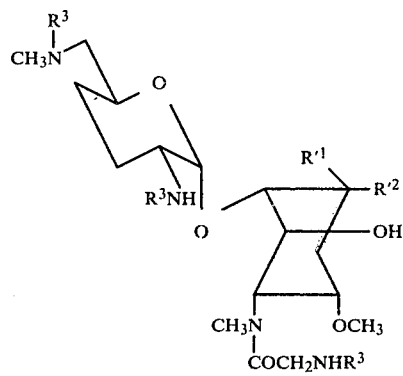

(I')

wherein $R^{1'}$ is a hydrogen atom and $R^{2'}$ is —$NHR^3$, or $R^{1'}$ is —$NHR^3$ and $R^{2'}$ is a hydrogen atom, and one, two, three or four of the $R^3$ groups represent(s) —CHRSO₃M and the other $R^3$ groups represent(s) a hydrogen atom where R is a hydrogen atom, a 1-4 carbon alkyl group, a methoxymethyl, monochloromethyl or dichloromethyl substituted alkyl group, a phenyl group or a p-methoxy or o-hydroxy substituted phenyl group, and M is a hydrogen atom, an ammonium cation, an alkali metal atom or an alkaline earth metal atom.

2. A compound according to claim 1, which is istamycin A-di-N-methanesulfonic acid disodium salt of the formula (I') where $R^{1'}$ is a hydrogen atom, $R^{2'}$ is —$NHR^3$, two $R^3$ groups represent —$CH_2SO_3Na$ and the remaining two $R^3$ groups represent a hydrogen atom.

3. A compound according to claim 1, which is istamycin A-tri-N-methanesulfonic acid trisodium salt of the formula (I') where $R^{1'}$ is a hydrogen atom, $R^{2'}$ is —$NHR^3$, three $R^3$ groups represent —$CH_2SO_3Na$ and the remaining one $R^3$ group represents a hydrogen atom.

4. A compound according to claim 1, which is istamycin A-tetra-N-methanesulfonic acid tetrasodium salt of the formula (I') where $R^{1'}$ is a hydrogen atom, $R^{2'}$ is —$NHR^3$, and all four $R^3$ groups represent —$CH_2SO_3Na$.

5. A compound according to claim 1, which is istamycin B-di-N-methanesulfonic acid disodium salt of the formula (I') where $R^{1'}$ is —$NHR^3$, $R^{2'}$ is a hydrogen atom, two $R^3$ groups represent —$CH_2SO_3Na$ and the remaining two $R^3$ groups represent a hydrogen atom.

6. A compound according to claim 1, which is istamycin B-tri-N-methanesulfonic acid trisodium salt of the formula (I') where $R^{1'}$ is —$NHR^3$, $R^{2'}$ is a hydrogen atom, three $R^3$ groups represent —$CH_2SO_3Na$ and the remaining one $R^3$ group represents a hydrogen atom.

7. A compound according to claim 1, which is istamycin B-tetra-N-methanesulfonic acid tetrasodium salt of the formula (I') where $R^{1'}$ is —$NHR^3$, $R^{2'}$ is a hydrogen atom, and all four $R^3$ groups represent —$CH_2SO_3Na$.

8. An antibacterial pharmaceutical composition for treating bacterial infections in a living animal, comprising an antibacterially effective amount of a compound according to claim 1, in combination with a pharmaceutically acceptable carrier therefor.

* * * * *